US012697295B2

(12) United States Patent
Liu et al.

(10) Patent No.: US 12,697,295 B2
(45) Date of Patent: Aug. 4, 2026

(54) COSMETIC COMPOSITIONS

(71) Applicant: L'ORÉAL, Paris (FR)

(72) Inventors: Xuefei Liu, Edison, NJ (US); Hy Si Bui, Piscataway, NJ (US); Ritesh Kumar Sinha, Linden, NJ (US)

(73) Assignee: L'ORÉAL, Paris (FR)

( * ) Notice: Subject to any disclaimer, the term of this patent is extended or adjusted under 35 U.S.C. 154(b) by 406 days.

(21) Appl. No.: 18/543,419

(22) Filed: Dec. 18, 2023

(65) Prior Publication Data

US 2025/0195391 A1      Jun. 19, 2025

(51) Int. Cl.
*A61K 8/81*        (2006.01)
*A61K 8/31*        (2006.01)
*A61K 8/92*        (2006.01)
*A61Q 1/06*        (2006.01)

(52) U.S. Cl.
CPC .............. *A61K 8/8152* (2013.01); *A61K 8/31* (2013.01); *A61K 8/92* (2013.01); *A61Q 1/06* (2013.01)

(58) Field of Classification Search
None
See application file for complete search history.

(56) References Cited

U.S. PATENT DOCUMENTS

| | | |
|---|---|---|
| 5,698,139 A | 12/1997 | Alper |
| 9,320,689 B2 | 4/2016 | Cassin et al. |
| 2022/0249342 A1* | 8/2022 | Mitra ...................... A61Q 1/14 |

FOREIGN PATENT DOCUMENTS

EP            0871593  B1    11/2004

* cited by examiner

*Primary Examiner* — Danah Al-Awadi
(74) *Attorney, Agent, or Firm* — Meagher Emanuel Laks Goldberg & Liao LLP

(57)            ABSTRACT

A cosmetic makeup composition may be provided. The cosmetic composition may include a reaction product of an acrylate and a natural or food-derived oil. The composition may include a dispersion of a hydrocarbon oil and a non-silicone polymer, where a ratio (R1) of the concentration of the non-silicone polymer to the reaction product is $R1>1$, such as $2 \leq R1 \leq 5$. The composition product may include a solvent. The composition may include a pigment. The natural or food-derived oil may be linseed oil. The non-silicone polymer may be a non-crosslinked non-silicone polymer, such as a copolymer of alkyl acrylate and a bicyclic terpene derivative, such as isobornyl acrylate.

11 Claims, No Drawings

COSMETIC COMPOSITIONS

TECHNICAL FIELD

The present disclosure is drawn to cosmetic compositions, and specifically to cosmetic compositions with improved tack, wear, and shine.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Cosmetic compositions, particularly such as those used on nails or lips, must not only provide desirable aesthetics when first applied, but must also survive exposure to various materials over the course of a day. For example, lip compositions may be expected to have a high degree of shine for hours, even after exposure to water, oils, or acids.

BRIEF SUMMARY

Various deficiencies in the prior art are addressed below by the disclosed compositions of matter and techniques.

In various aspects, a cosmetic makeup composition (such as a liquid lip composition, or a cosmetic composition for nails) may be provided. The cosmetic composition may include a reaction product of a natural or food-derived oil and a methacrylate or acrylate polymer. The composition may include a hydrocarbon oil. The composition may include a non-silicone polymer, where a ratio (R1) of the concentration of the non-silicone polymer to the reaction product is R1>1, such as 2≤R1≤5. The composition product may include a solvent. The composition may include a pigment.

The natural or food-derived oil may be linseed oil.

The non-silicone polymer may be a non-crosslinked non-silicone polymer. The non-crosslinked non-silicone polymer may be a copolymer of alkyl acrylate and a bicyclic terpene derivative. The bicyclic terpene derivative may be isobornyl acrylate.

The hydrocarbon oil and the non-silicone polymer may be provided as a dispersion.

The solvent may be a hydrocarbon oil. The pigment may be a plurality of pigments.

In various aspects, a method may be provided for coloring lips. The method may include providing a cosmetic makeup composition as disclosed herein, and applying the cosmetic makeup composition to lips.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

As used herein, the term "free of (a component)" indicates the compositions do not contain the component in any measurable degree by standard means. As used herein, the term "substantially free of (a component)" indicates that the compositions contain no appreciable amount of the component, for example, no more than about 1% by weight, or no more than about 0.5% by weight, or no more than about 0.3% by weight, such as no more than about 0.1% by weight, based on the weight of the system or composition comprising the system and/or the oxidizing composition according to embodiments of the disclosure.

In various aspects, a cosmetic makeup composition may be provided. The cosmetic makeup composition may be applied to keratinous tissue, such as hair, skin, or nails. The cosmetic makeup composition may be a liquid lip composition (e.g., a composition that remains flowable at room temperature).

Reaction Product

The composition may include a reaction product of a natural or food-derived oil and a methacrylate or acrylate polymer. The cosmetic composition may include a reaction product of a poly(isobutyl methacrylate) and a natural or food-derived oil. In particular, the natural or food-derived oil may be a drying oil, preferably linseed oil. Preferably, the reaction product is under the trade name MYCELX® from Mycelx Technologies Corporation of Gainesville, Georgia. See U.S. Pat. No. 5,698,139 and EP 0 871 593 B1 for a description of MYCELX® materials.

The reaction product may be a reaction product of a natural or food-derived oil and a methacrylate or acrylate polymer. The reaction product may be a reaction product of a natural or food-derived oil and a methacrylate polymer. The natural or food-derived oil may be a drying oil or semi-drying oil, preferably wherein the natural or food-derived oil is linseed oil, sunflower oil, tung oil, fish oil, cottonseed oil, soybean oil, or a combination thereof. The natural or food-derived oil may be linseed oil. The polymer may be derived from monomers including, e.g., isobutyl methacrylate, methyl methacrylate, ethyl methacrylate, n-butyl methacrylate, or a combination thereof. The polymer may be an isobutyl methacrylate polymer. The reaction product may be a reaction product of linseed oil and poly (isobutyl methacrylate).

The reaction product may form, e.g., a hydrophobic polymer.

The reaction product may be present in a total amount of no more than 20% by weight of the composition. The reaction product may be present in a total amount of no more than 19% by weight of the composition. The reaction product may be present in a total amount of no more than 18% by weight of the composition. The reaction product may be present in a total amount of no more than 17% by weight of the composition. The reaction product may be present in a total amount of no more than 16% by weight of the composition. The reaction product may be present in a total amount of no more than 15% by weight of the composition. The reaction product may be present in a total amount of no more than 14% by weight of the composition. The reaction product may be present in a total amount of no more than 13% by weight of the composition. The reaction product may be present in a total amount of no more than 12% by weight of the composition. The reaction product may be present in a total amount of no more than 11% by weight of the composition. The reaction product may be present in a total amount of at least 0.5% by weight of the composition. The reaction product may be present in a total amount of at least 1% by weight of the composition. The reaction product may be present in a total amount of at least 2% by weight of the composition. The reaction product may be present in a total amount of at least 3% by weight of the composition. The reaction product may be present in a total amount of at least 4% by weight of the composition. The reaction product may be present in a total amount of at least 5% by weight of the composition. The reaction product may be present in a total amount of at least 6% by weight of the composition. The reaction product may be present in a total amount of at least 7% by weight of the composition. The reaction product may be present in a total amount of at least 8% by weight of the composition. The reaction product may be present in a total amount of at least 9% by weight of the composition.

Hydrocarbon Oil

The composition may include a first hydrocarbon oil.

The term "hydrocarbon oil" is understood to mean an oil consisting of carbon and hydrogen atoms. The first hydrocarbon oil may have from 8 to 16 carbon atoms. The first hydrocarbon oil may be a branched $C_8$-$C_{16}$ alkane, such as $C_8$-$C_{16}$ isoalkanes of petroleum origin (also known as isoparaffins), such as isododecane (also known as 2,2,4,4, 6-pentamethylheptane), isodecane, and isohexadecane. The first hydrocarbon oil may be a linear $C_8$-$C_{16}$ alkane, such as n-dodecane ($C_{12}$) and n-tetradecane ($C_{14}$).

The first hydrocarbon oil may be present in the composition in a total amount of no more than 60% by weight of the composition. The first hydrocarbon oil may be present in the composition in a total amount of no more than 55% by weight of the composition. The first hydrocarbon oil may be present in the composition in a total amount of no more than 50% by weight of the composition. The first hydrocarbon oil may be present in the composition in a total amount of no more than 45% by weight of the composition. The first hydrocarbon oil may be present in the composition in a total amount of no more than 40% by weight of the composition. The first hydrocarbon oil may be present in the composition in a total amount of at least 1% by weight of the composition. The first hydrocarbon oil may be present in the composition in a total amount of at least 5% by weight of the composition. The first hydrocarbon oil may be present in the composition in a total amount of at least 10% by weight of the composition. The first hydrocarbon oil may be present in the composition in a total amount of at least 15% by weight of the composition. The first hydrocarbon oil may be present in the composition in a total amount of at least 20% by weight of the composition. The first hydrocarbon oil may be present in the composition in a total amount of at least 25% by weight of the composition. The first hydrocarbon oil may be present in the composition in a total amount of at least 30% by weight of the composition.

In some embodiments, the first hydrocarbon oil may be a single oil. In some embodiments, the first hydrocarbon oil may be a plurality of hydrocarbon oils.

Non-Silicone Polymer

The composition may include a non-silicone polymer. The non-silicone polymer may be a non-crosslinked non-silicone polymer. The non-crosslinked non-silicone polymer may be a copolymer of alkyl acrylate and a bicyclic terpene derivative. The bicyclic terpene derivative may be isobornyl acrylate. A preferred non-cross-linked non-silicone polymer may be an acrylates/isobornyl acrylate copolymer.

The non-silicone polymer may be present in the composition in a total amount of no more than 45% by weight of the composition. The non-silicone polymer may be present in the composition in a total amount of no more than 40% by weight of the composition. The non-silicone polymer may be present in the composition in a total amount of no more than 35% by weight of the composition. The non-silicone polymer may be present in the composition in a total amount of at least 0.1% by weight of the composition. The non-silicone polymer may be present in the composition in a total amount of at least 1% by weight of the composition. The non-silicone polymer may be present in the composition in a total amount of at least 5% by weight of the composition. The non-silicone polymer may be present in the composition in a total amount of at least 10% by weight of the composition. The non-silicone polymer may be present in the composition in a total amount of at least 15% by weight of the composition. The non-silicone polymer may be present in the composition in a total amount of at least 20% by weight of the composition. The non-silicone polymer may be present in the composition in a total amount of at least 25% by weight of the composition. The non-silicone polymer may be present in the composition in a total amount of at least 30% by weight of the composition.

A ratio (R1) of the concentration of the non-silicone polymer to the reaction product is R1>1. The ratio R1 may be at least 1.25. The ratio R1 may be at least 1.5. The ratio R1 may be at least 1.75. The ratio R1 may be at least 2. The ratio R1 may be no more than 10. The ratio R1 may be no more than 9. The ratio R1 may be no more than 8. The ratio R1 may be no more than 7. The ratio R1 may be no more than 6. The ratio R/may be no more than 5. In some embodiments, the ratio R1 may be 2≤R1≤5.

A ratio (R2) of the concentration of the non-silicone polymer to the first hydrocarbon oil. The ratio R2 may be no more than 1. The ratio R2 may be no more than 0.95. The ratio R2 may be no more than 0.9. The ratio R2 may be at least 0.5. The ratio R2 may be at least 0.6. The ratio R2 may be at least 0.7. The ratio R2 may be at least 0.8.

The hydrocarbon oil and the non-silicone polymer may be provided separately. The hydrocarbon oil and the non-silicone polymer may be provided as a dispersion.

Solvent

The composition product may include a solvent. The solvent may be an oil. The solvent may be a second hydrocarbon oil. The solvent may be a fatty ester. In some cases, the one or more fatty esters may be a glycerol ester of fatty acids or glyceryl esters (or glycerol fatty esters), for example, glyceryl monomyristate, glyceryl monopalmitate, glyceryl monostearate, glyceryl isostearate, glyceryl monooleate, glyceryl dioleate, glyceryl distearate, glyceryl laurate, trilaurin, triarachidin, tribehenin, tricaprin, tricaprylin, caprylic/capric triglyceride, trierucin, triheptanoin, triheptylundecanoin, triisononanoin, triisopalmitin, triisostearin, trilinolein, trimyristin, trioctanoin, triolein, tripalmitin, tripalmitolein, triricinolein, tristearin, triundecanoin, and mixtures thereof.

The solvent may have a polarity index of less than 24 mN/m. The polarity index refers to the polarity or the surface tension (in $10^{-3}$ Newton/meter) of a material, which is determined with, e.g., a ring tensiometer using well-understood techniques.

The solvent may include at least one volatile solvent.

In certain embodiments, the expression "volatile solvent" means any non-aqueous compound capable of evaporating on contact with the skin or the lips in less than one hour at room temperature and atmospheric pressure. In certain other embodiments "volatile solvent" means any non-aqueous compound having a flash point of less than about 120° C., such as less than about 100° C., such as from about 40° C. to about 100° C.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of ISOPAR™ fluids or PERMETHYL® fluids, the $C_8$ to $C_{16}$ branched esters such as isohexyl or isodecyl neopentanoate, alcohols, and their mixtures.

Examples of volatile hydrocarbon-based oils include, but are not limited to those given in Table 1 below.

TABLE 1

| Compound | Flash Point (° C.) |
| --- | --- |
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |

6

TABLE 2-continued

| Compound | Flash Point (° C.) | Viscosity (cSt) |
| --- | --- | --- |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (5 cSt) from Dow Corning | 134 | 5 |
| PDMS DC 200 (3 St) from Dow Corning | 102 | 3 |

The solvent may be present in the composition in a total amount of no more than 50% by weight of the composition. The solvent may be present in the composition in a total amount of no more than 40% by weight of the composition. The solvent may be present in the composition in a total amount of no more than 30% by weight of the composition. The solvent may be present in the composition in a total amount of no more than 25% by weight of the composition. The solvent may be present in the composition in a total amount of no more than 20% by weight of the composition. The solvent may be present in the composition in a total amount of no more than 15% by weight of the composition. The solvent may be present in the composition in a total amount of no more than 10% by weight of the composition. The solvent may be present in the composition in a total amount of at least 1% by weight of the composition. The solvent may be present in the composition in a total amount of at least 3% by weight of the composition. The solvent may be present in the composition in a total amount of at least 5% by weight of the composition. The solvent may be present in the composition in a total amount of at least 10% by weight of the composition.

Colorants

The composition may include at least one cosmetically acceptable colorant, such as a pigment or dyestuff.

The term "pigment" means any pigment that gives color to keratin materials. Their solubility in water at 25° C. and atmospheric pressure (760 mmHg) is less than 0.05% by weight, preferably less than 0.01%.

Examples of suitable pigments include, but are not limited to, inorganic pigments, organic pigments, lakes, pearlescent pigments, iridescent or optically variable pigments, and mixtures thereof. The pigments may be chosen from the organic and/or mineral pigments known in the art. The pigments may be in the form of powder or of pigmentary paste. They may be coated or uncoated. Said pigments may optionally be surface-treated within the scope of the present invention but are not limited to treatments such as silicones, perfluorinated compounds, lecithin, and amino acids.

The pigments may be chosen, for example, from inorganic pigments, organic pigments, lakes, pigments with special effects such as nacres or glitter flakes, and mixtures thereof. Non-limiting examples of inorganic pigments include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The pigment may be an inorganic pigment. The term "inorganic pigment" refers to any pigment that satisfies the definition in Ullmann's encyclopedia in the chapter on inorganic pigments. Non-limiting examples include iron oxides, chromium oxides, manganese violet, ultramarine blue, chromium hydrate, ferric blue and titanium oxide.

The pigment may be an organic pigment. The term "organic pigment" refers to any pigment that satisfies the definition in Ullmann's encyclopedia in the chapter on organic pigments. Non-limiting examples include nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds.

In particular, the white or colored organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and pigments obtained by oxidative polymerization of indole or phenolic derivatives. Non-limiting examples of organic pigments and lakes include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

The pigments in accordance with the invention may also be in the form of composite pigments. These composite pigments may be compounds especially of particles comprising a inorganic core, at least one binder for ensuring the binding of the organic pigments to the core, and at least one organic pigment at least partially covering the core.

The organic pigment may also be a lake. The term "lake" refers dyes adsorbed onto insoluble particles, the assembly thus obtained remaining insoluble during use.

The inorganic substrates onto which the dyes are adsorbed are, for example, alumina, silica, calcium sodium borosilicate or calcium aluminum borosilicate, and aluminum.

Among the dyes, mention may be made of cochineal carmine. Non-limiting examples of dyes include: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090). An example of a lake is D&C Red 7 (CI 15 850:1).

The pigment may also be a pigment with special effects. The term "pigments with special effects" refers pigments that generally create a non-uniform colored appearance (characterized by a certain shade, a certain vivacity and a certain lightness) that changes as a function of the conditions of observation (light, temperature, observation angles, etc.). They thus contrast with colored pigments that afford a standard uniform opaque, semi-transparent or transparent shade.

Several types of pigment with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery color or tint.

Non-limiting examples of nacres include gold-colored nacres sold especially by the company Engelhard under the name Gold 222C (a CLOISONNE® pigment), Sparkle gold (a TIMICA® pigment), Gold 4504 (a CHROMA-LITE® pigment) and Monarch gold 233X (a CLOISONNE® pigment); the bronze nacres sold especially by the company Merck under the name Bronze fine (17384) (a COLORONA® pigment) and Bronze (17353) (a COLORONA® pigment), by the company Eckart under the name PRESTIGE™ Bronze pigment and by the company Engelhard under the name Super bronze (a CLOISONNE® pigment); the orange nacres sold especially by the company Engelhard under the name Orange 363C (a CLOISONNE® pigment) and Orange MCR 101 and by the company Merck under the name Passion orange (a COLORONA® pigment) and Matte orange (17449); the brown nacres sold especially by the company Engelhard under the name Nu-antique copper 340XB (a CLOISONNE® pigment) and Brown CL4509 (a CHROMA-LITER pigment); the nacres with a copper tint sold especially by the company Engelhard under the name Copper 340A (a TIMICA® pigment) and by the company Eckart under the name Prestige Copper; the nacres with a red tint sold especially by the company Merck under the name Sienna fine (17386) (a COLORONA® pigment); the nacres with a yellow tint sold especially by the company Engelhard under the name Yellow (4502) (a CHROMA-LITE® pigment); the red nacres with a gold tint sold especially by the company Engelhard under the name Sunstone G012 (a GEMTONE® pigment); the black nacres with a gold tint sold especially by the company Engelhard under the name Nu antique bronze 240 AB (a TIMICA® pigment), the blue nacres sold especially by the company Merck under the name Matte blue (17433), Dark Blue (117324) (a COLORONA® pigment), the white nacres with a silvery tint sold especially by the company Merck under the name XIRONA® Silver pigment, and the golden-green pink-orange nacres sold especially by the company Merck under the name Indian summer (a XIRONA® pigment), and mixtures thereof.

In addition to nacres on a mica support, multilayer pigments based on synthetic substrates such as alumina, silica, sodium calcium borosilicate or calcium aluminum borosilicate, and aluminum, may be envisaged.

Non-limiting examples of pearlescent pigments include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Mention may also be made of pigments with an interference effect that are not fixed onto a substrate, for instance liquid crystals or holographic interference glitter flakes. Pigments with special effects also comprise fluorescent pigments, whether these are substances that are fluorescent in daylight or that produce an ultraviolet fluorescence, phosphorescent pigments, photochromic pigments, thermochromic pigments and quantum dots.

The variety of pigments that may be used in the present invention makes it possible to obtain a wide range of colors, and also particular optical effects such as metallic effects or interference effects.

The effective diameter of the pigment particles may generally be between 10 nm and 200 μm, such as between 20 nm and 80 μm, such as between 30 nm and 50 μm.

The pigment may be present in a total amount of no more than 20% by weight of the composition. The pigment may be present in a total amount of no more than 15% by weight of the composition. The pigment may be present in a total amount of no more than 10% by weight of the composition. The pigment may be present in a total amount of no more than 8% by weight of the composition. The pigment may be present in a total amount of no more than 6% by weight of the composition. The pigment may be present in a total amount of no more than 5% by weight of the composition. The pigment may be present in a total amount of at least 0.1% by weight of the composition. The pigment may be present in a total amount of at least 1% by weight of the composition. The pigment may be present in a total amount of at least 2% by weight of the composition. The pigment may be present in a total amount of at least 3% by weight of the composition. The pigment may be present in a total amount of at least 4% by weight of the composition. The pigment may be present in a total amount of at least 5% by weight of the composition.

The pigment may be a single pigment. The pigment may be a plurality of pigments.

Filler

The composition may include one or more fillers. Non-limiting examples of fillers include silica powder; talc; polyamide particles and especially those sold under the name ORGASOL® powders by the company Atochem; polyethylene powders; microspheres based on acrylic copolymers, such as those based on ethylene glycol dimethacrylate/lauryl methacrylate copolymer sold by the company Dow Corning under the name POLYTRAP® systems; expanded powders such as hollow microspheres and especially the microspheres sold under the name EXPANCEL® thermoplastic microspheres by the company Kemanord Plast or under the name MICROSPHERE® F 80 ED microcapsules by the company Matsumoto; powders of natural organic materials such as crosslinked or noncrosslinked corn starch, wheat starch or rice starch, such as the powders of starch crosslinked with octenyl succinate anhydride, sold under the name DRY-FLOR starch by the company National Starch; silicone resin microbeads such as those sold under the name TOSPEARL® microspheres by the company Toshiba Silicone; clays (bentone, laponite, saponite, etc.); and mixtures thereof.

In one notable embodiment, the other fillers present in the composition include a swellable clay. By "swellable clay" it is meant a clay material that is capable of swelling in water. An example of a swellable clay are smectite clays. The crystal structure of the smectite group, is an octahedral alumina sheet between two tetrahedral silica sheets. In one notable embodiment, the swellable clay is bentonite. Bentonite is a rock formed of highly colloidal and plastic clays composed mainly of montmorillonite, a clay mineral of the smectite group, and is produced by in situ devitrification of volcanic ash. In addition to montmorillonite, bentonite may contain feldspar, cristobalite, and crystalline quartz. Bentonite has an ability to form thixotrophic gels with water, an ability to absorb large quantities of water. Variations in interstitial water and exchangeable cations in the interlayer space affect the properties of bentonite and thus the commercial uses of the different types of bentonite.

One notable swellable clay suitable for use in the composition is BENTONE GEL® ISD V dispersion, commercially available from Elementis Specialties, East Windsor, New Jersey. BENTONE GEL® GTCC V dispersion is a dispersion of organically (disterammonium) modified hectorite in isododecane with added propylene carbonate.

The fillers (e.g., swellable clay) may be present in the compositions of the present invention in an amount ranging from about 1% to about 10% by weight, such as from about 0.1%, 0.5%, or 1% by weight to about 2%, 3%, 5% or 10%, based on the total weight of the composition, including all ranges and subranges within these ranges. Propylene carbonate, if present, may be present in the compositions of the present invention in an amount ranging from about 0.25% to about 2% by weight, or, for example, in an amount such that the ratio by weight of swellable clay to propylene carbonate is about 2:1 to about 5:1.

While in certain embodiments, certain fillers such as hydrophobic silica aerogels may be included. In certain other embodiments, the compositions are substantially free of hydrophobic silica aerogels.

Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990. Silica aerogels, in general, have been disclosed in U.S. Pat. No. 9,320,689, the entire content of which is hereby incorporated by reference.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m2/g.

Mention may also be made of the aerogels sold by the company Cabot under the references Aerogel TLD 201, Aerogel OGD 201, Aerogel TLD 203, ENOVA® Aerogel MT 1100 silica aerogel, ENOVA® Aerogel MT 1200 silica aerogel.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 $m^2$/g.

The silica aerogel particles if used can be used in the inventive compositions from 0.1% to about 8% by weight, preferably from about 0.1%, 0.2%, or 0.5% to about 0.5%, 1% 2% or 5% by weight, all weights based on the weight of the composition as a whole.

The compositions of the present invention may include at least one cosmetically or dermatologically acceptable additive such as a thickener, a plasticizer, an antioxidant, an essential oil, a botanical extract, a fragrance, a preserving agent, a fragrance, a pasty fatty substance, a neutralizing agent, and a polymer, and cosmetically active agents and/or dermatological active agents such as, for example, emollients, moisturizers, vitamins, essential fatty acids and medicaments.

As per this invention, the additives are incorporated from about 0.01%, 0.5% or 1% to about 1%, 2%, or 5% by weight.

The compositions of the present invention are useful as compositions for making up the skin, in particular the lips.

Compositions may be made by methods known to those skilled in the art, such as by charging a vessel with one or more solvents or oil and adding various ingredients and mixing. Pigments may be pre-ground into a suspension or slurry prior to adding.

The composition may be free of water. The composition may be substantially free of water. The composition may be free of a surfactant. The composition may be substantially free of a cleansing material.

In various aspects, a method may be provided for coloring lips. The method may include providing a cosmetic makeup composition as disclosed herein, and applying the cosmetic makeup composition to lips.

Example 1

Sample stabilities were performed by considering different ratios (R1) of the non-silicone polymer to the reaction product. Samples were created as indicated in Table 1 below, with R1 ratios of 5 (S1), 2 (S3), 1 (S4), 0.5 (S5) and 0.2 (S6). Stabilities were visually checked after 24 hours, and after 2 weeks.

TABLE 1

| | | | Formulations | | |
|---|---|---|---|---|---|
| Material | S1 wt % | S3 wt % | S4 wt % | S5 wt % | S6 wt % |
| Acrylate/Isobornyl Acrylate Copolymer | 25 | 20 | 15 | 10 | 5 |
| Reaction Product | 5 | 10 | 15 | 20 | 25 |
| Isododecane | 60 | 60 | 60 | 60 | 60 |
| Caprylic/Capric Triglyceride | 10 | 10 | 10 | 10 | 10 |

After 24 hours, some signs of separation could be seen in S4 and S5, and separation had already occurred in S6. After 2 weeks, separation was visible in S4, S5, and S6, although S4 was borderline. No separation was seen in S1 or S3. Thus, it will be understood that preferably, the ratio R1 is greater than 1, and more preferably 2-5.

Example 2

The following formulations, in Table 2 below, were created to provide similar draw-down characteristics. Comparative 1 (C1) includes only the dispersion (with a hydrocarbon oil and a non-crosslinked non-silicone polymer), the solvent, and the pigment. Comparative 2 (C2) includes the MYCELX® reaction product, the hydrocarbon oil from the dispersion, the solvent, and the pigment. Comparative 3 (C3) has the hydrocarbon oil from the dispersion, but instead of the non-crosslinked non-silicone polymer, includes Acrylate/Dimethicone Copolymer (the active material in Shin-Etsu's KP-550 fluid), the solvent, and the pigment. Comparative 4 (C4) adds the same reaction product as C2 to C3.

Exemplary 1 (E1) adds the same reaction product as C2 to C1. E1 was chosen to have a ratio R1 of 3, but similar results occur at other ratios.

TABLE 1

| | | | Formulations | | |
|---|---|---|---|---|---|
| Material | C1 grams | C2 grams | C3 grams | C4 grams | E1 grams |
| Reaction Product | — | 7.5 | — | 7.5 | 7.5 |
| Isododecane | 25 | 25 | 37 | 37 | 25 |
| Acrylate/Isobornyl Acrylate Copolymer | 22.5 | — | — | — | 22.5 |
| Acrylate/Dimethicone Copolymer | — | — | 22.5 | 22.5 | — |
| Caprylic/Capric Triglyceride | 10 | 10 | 10 | 10 | 10 |
| Hydrophobically Treated Pigment (Red 7) | 6 | 6 | 6 | 6 | 6 |

Shine. To measure shine, films of each formulation were drawn down on byko-chart Black Scrub Panel P121-10N (BYK) with 1 mil draw down bars. The samples were left overnight, or until the films were dried down. The gloss was then measured using a BYK three-angle gloss meter. Results are shown in Table 3, below.

TABLE 3

| | | | Shine Results | | |
|---|---|---|---|---|---|
| Angle | C1 Gloss Units | C2 Gloss Units | C3 Gloss Units | C4 Gloss Units | E1 Gloss Units |
| 20° | 21.7 | 56.5 | 55.8 | 63.6 | 30.1 |
| 60° | 61.7 | 72.8 | 73.5 | 75.9 | 69.9 |
| 85° | 62 | 71.2 | 74.1 | 73.1 | 66.4 |

As seen, the addition of the reaction product increases shine. However, it is noted that adding the reaction product to the oil/non-crosslinked non-silicone polymer dispersion (e.g., comparing C1 to E1), the increase in shine is substantial at 20°, 60°, and 85°, and statistically significant. When adding the reaction product to the oil/silicone polymer dispersion (e.g., comparing C3 and C4), an increase in shine is only really seen at 20°, with any change at 60° or 85° being statistically insignificant.

Tack/Adhesion. To measure tack/adhesion, compositions were drawn down on byko-chart Black Scrub Panel P121-10N (BYK) with 1 mil draw down bars. Tack was then measured by: securing the substrate, using a ½ inch ball probe to press down at 200 gram force for 10 seconds, raising the ball probe at 10 mm/second perpendicular from the substrate, and measure the tack by extracting the peak force when the ball probe is detached from the surface. The average tack (in grams of force) over 5 measurements can be seen in Table 4.

TABLE 4

| | | Tack/Adhesion | | | |
|---|---|---|---|---|---|
| | C1 | C2 | C3 | C4 | E1 |
| Tack | 11.69 | 2.97 | 6.34 | 17.58 | 55.45 |

The disclosed oil/non-silicone dispersion alone (C1) has a moderate tack. The reaction product alone (C2) has very little tack. The combination of the disclosed oil/non-silicone dispersion and the reaction product (E1) has a synergistic effect on tack, indicating more adhesion, which is much more significant than the combination of the oil/silicone polymer and the reaction product (e.g., comparing C3 and C4). The change from C3 to C4 is an increase in tack by a factor of about 2.8. The increase from C1 to E1 is a factor of 4.7. This is a surprising and unexpected benefit of this combination.

Solvent resistance. To measure solvent resistance, each formulation was applied to a Black Scrub Panel P121-10N #5015 byko-chart using a 1 mil draw down bar. The films were allowed to dry overnight at 35° C. and 60% RH. To evaluate the samples, 6 drops of fluids (two drops of olive oil, two drops of artificial saliva, and two drops of 2% acetic acid) were placed on different sections of the film, and then allowed to stand for 10 minutes. The amount of material removed by the drops themselves was evaluated. In addition, a cotton pad was used to gently wipe off each drop 15 times. It was then observed how much product wipes onto the cotton pad and how/if the product moves on the byko-chart substrate. The ratings used a scale of 0 (no removal) to 3 (substantial removal).

TABLE 5

| Solvent Resistance | | | | | |
| --- | --- | --- | --- | --- | --- |
| | C1 | C2 | C3 | C4 | E1 |
| Olive Oil | 1.5 | 2.5 | 1.5 | 1 | 1 |
| Acetic Acid | 1 | 2 | 1.25 | 1 | 0.5 |
| Artificial Saliva | 0.5 | 1.25 | .75 | 0.25 | 0.25 |

As seen, the addition of the reaction polymer improved wear/solvent resistance over control formulas without the reaction polymer. Compare, e.g., C1 to E1, and C3 to C4.

Various modifications may be made to the systems, methods, apparatus, mechanisms, techniques, and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof. As such, the appropriate scope of the invention is to be determined according to the claims.

What is claimed is:

1. A cosmetic makeup composition, comprising:
a reaction product of a natural or food-derived oil and a methacrylate or acrylate polymer;
a hydrocarbon oil;
a non-silicone polymer, where a ratio (R1) of the concentration of the non-silicone polymer to the reaction product is R1>1;
a solvent; and
a pigment.

2. The cosmetic makeup composition of claim 1, wherein $2 \leq R1 \leq 5$.

3. The cosmetic makeup composition of claim 1, wherein the natural or food-derived oil is linseed oil.

4. The cosmetic makeup composition of claim 1, wherein the hydrocarbon oil and the non-silicone polymer are provided as a dispersion.

5. The cosmetic makeup composition of claim 1, wherein the non-silicone polymer is a non-crosslinked non-silicone polymer.

6. The cosmetic makeup composition of claim 5, wherein the non-crosslinked non-silicone polymer is a copolymer of alkyl acrylate and a bicyclic terpene derivative.

7. The cosmetic makeup composition of claim 6, wherein the bicyclic terpene derivative is isobornyl acrylate.

8. The cosmetic makeup composition of claim 1, wherein the cosmetic makeup composition is a liquid lip composition.

9. The cosmetic makeup composition of claim 1, wherein the solvent is a hydrocarbon oil.

10. The cosmetic makeup composition of claim 1, wherein the pigment is a plurality of pigments.

11. A method for coloring lips, comprising:
providing a cosmetic makeup composition of claim 1; and
applying the cosmetic makeup composition to lips.

* * * * *